United States Patent
Hudlicky et al.

(10) Patent No.: US 9,700,813 B2
(45) Date of Patent: Jul. 11, 2017

(54) METHODS AND APPARATUS FOR TIME-PULSED CHROMATOGRAPHY

(71) Applicants: Tomas Hudlicky, St. Catharines (CA); Ian David Brindle, St. Catharines (CA); Mary Ann Endoma-Arias, St. Catharines (CA)

(72) Inventors: Tomas Hudlicky, St. Catharines (CA); Ian David Brindle, St. Catharines (CA); Mary Ann Endoma-Arias, St. Catharines (CA)

( * ) Notice: Subject to any disclaimer, the term of this patent is extended or adjusted under 35 U.S.C. 154(b) by 85 days.

(21) Appl. No.: 14/269,336

(22) Filed: May 5, 2014

(65) Prior Publication Data

US 2014/0326670 A1    Nov. 6, 2014

Related U.S. Application Data

(60) Provisional application No. 61/819,819, filed on May 6, 2013, provisional application No. 61/899,404, filed on Nov. 4, 2013.

(51) Int. Cl.
| | |
|---|---|
| *B01D 15/16* | (2006.01) |
| *B01D 15/18* | (2006.01) |
| *G01N 30/38* | (2006.01) |
| *G01N 30/32* | (2006.01) |
| *B01D 15/22* | (2006.01) |
| *G01N 30/28* | (2006.01) |
| *B01D 15/14* | (2006.01) |

(52) U.S. Cl.
CPC ......... *B01D 15/163* (2013.01); *B01D 15/18* (2013.01); *G01N 30/32* (2013.01); *B01D 15/14* (2013.01); *G01N 30/28* (2013.01); *G01N 2030/324* (2013.01)

(58) Field of Classification Search
CPC ........ B01D 15/10; B01D 15/18; B01D 15/16; B01D 15/163; B01D 15/14; G01N 30/50; G01N 30/26; G01N 30/28; G01N 30/32; G01N 2030/522; G01N 2030/322; G01N 2030/324; G01N 2030/326
USPC .............................................. 210/656, 198.2
See application file for complete search history.

(56) References Cited

U.S. PATENT DOCUMENTS

| | | | |
|---|---|---|---|
| 3,220,164 A | 11/1965 | Golay | |
| 4,753,775 A * | 6/1988 | Ebersole | ................. B01L 3/021 422/400 |
| 5,096,471 A * | 3/1992 | Sacks | ..................... G01N 30/40 95/87 |
| 7,240,572 B2 * | 7/2007 | Pitt | ......................... B01L 3/502 73/863.21 |
| 2005/0182257 A1 | 8/2005 | Antonini | |

(Continued)

OTHER PUBLICATIONS

Targett et al. Vacuum liquid chromatography: An alternative to common chromatographic methods. J. Org. Chem. vol. 44, No. 26 (1979) 4962-4964.*

(Continued)

*Primary Examiner* — Katherine Zalasky
(74) *Attorney, Agent, or Firm* — Bereskin & Parr LLP/S.E.N.C.R.L., s.r.l.

(57) ABSTRACT

The present disclosure relates to methods for the chromatographic separation of two or more sample components using a column while applying a time-pulsed pressure differential to the column and to apparatus for use in the same.

20 Claims, 4 Drawing Sheets

(56) References Cited

U.S. PATENT DOCUMENTS

| | | | |
|---|---|---|---|
| 2008/0006578 A1* | 1/2008 | Sims | G01N 30/28 210/639 |
| 2010/0065495 A1 | 3/2010 | Shreve et al. | |
| 2013/0015138 A1 | 1/2013 | Schlake et al. | |

OTHER PUBLICATIONS

Fisher Scientific, "Vacuum Pumps," available at <http://www.thermofishersci.in/lit/Fisherbrand%20Vacuum%20Pumps.pdf>, accessed Aug. 22, 2016.*

* cited by examiner

METHODS AND APPARATUS FOR TIME-PULSED CHROMATOGRAPHY

CROSS-REFERENCE TO RELATED APPLICATIONS

The present application claims the benefit of priority from co-pending U.S. provisional application No. 61/819,819 filed on May 6, 2013 and 61/899,404 filed on Nov. 4, 2013, respectively, the contents of each of which are incorporated herein by reference in their entirety.

FIELD

The present disclosure relates to methods and apparatuses for the chromatographic separation of two or more sample components. In particular, the present disclosure relates to methods for the chromatographic separation of the two or more sample components using a column while applying a time-pulsed pressure differential to the column and to an apparatus for use in the same.

BACKGROUND

The separation of mixtures by adsorption on chemically inert surfaces was invented (or discovered) more than 150 years ago.[1,2] Over the past 50 years, column chromatography methods have undergone numerous improvements. One of the major innovations in this field was the development of flash column chromatography reported in 1978 by Still.[3] As of November 2012, this paper by Still et al. has been cited more than 3100 times. Other forms of column chromatography such dry column chromatography[4] and vacuum chromatography[5] have also been developed for separation. In addition, methods that change some of the physical parameters of separation and solvent flow, such as spinning disk chromatography (Chromatotron™) have been used.

SUMMARY

In the present disclosure, a new technique of chromatography under pressure, with intentional time-pulsed interruptions in the pressure that have a marked effect on difficult separations has been demonstrated. The technique uses less solvent and takes less time than known methods. As shown by the analysis of principles involved, this technique should also be applicable to medium- and high-pressure chromatography where pressure would be applied to the stationary phase from two directions at particular time intervals.

Accordingly, the present disclosure includes a method for chromatographic separation of two or more sample components comprising: applying at least one time-pulsed pressure differential to a column during chromatographic separation of two or more sample components.

In an embodiment, the method for chromatographic separation of two or more sample components comprises:
a) introducing a sample into a column, the column having at least one inlet for receiving a liquid mobile phase at a first end of the column, at least one outlet for eluting a sample rich liquid mobile phase at a second end of the column, a stationary phase housed between the at least one inlet and the at least one outlet, the sample comprising the two or more sample components and being introduced into the first end of the column so that it is in contact with the stationary phase; and
b) contacting the sample and the stationary phase with the liquid mobile phase and obtaining the sample rich liquid mobile phase while applying at least one time-pulsed pressure differential to the column.

In an embodiment of the present disclosure, applying the time-pulsed pressure differential to the column comprises:
a) applying a vacuum to the column using a vacuum source coupled to the column at a position below the stationary phase;
b) stopping the vacuum applied to the column;
c) reapplying the vacuum to the column; and
d) optionally repeating b)-c) until separation of the two or more sample components is at least substantially complete.

In another embodiment of the present disclosure, applying the time-pulsed pressure differential to the column comprises:
a) applying a first pressure to the column using a first pressure source coupled to the column at a position above the stationary phase;
b) stopping the first pressure applied to the column and applying a second pressure to the column using a second pressure source coupled to the column at a position below the stationary phase;
c) stopping the second pressure applied to the column and reapplying the first pressure applied to the column; and
d) optionally repeating b)-c) until separation of the two or more sample components is at least substantially complete.

The present disclosure also includes a chromatography apparatus comprising: a column having an inlet, an outlet and a pump, wherein the pump is configured to apply at least one time-pulsed pressure differential to the inlet and/or the outlet of the column.

In an embodiment, the apparatus for time-pulsed chromatography comprises:
a column for separating a sample comprising two or more sample components, the column having at least one inlet, at least one outlet, a stationary phase positioned between the at least one inlet and the at least one outlet; and
a pump,
wherein the pump is configured to apply at least one time-pulsed pressure differential to the at least one inlet and/or the at least one outlet of the column.

In an embodiment of the present disclosure, the pump comprises: a vacuum source fluidly connectable to the column at a position below the stationary phase, the vacuum source having a first state which applies a vacuum to the column and a second state which stops application of the vacuum to the column; and an actuator for switching the vacuum source between the first state and the second state.

In another embodiment, the pump comprises: a first pressure source fluidly connectable to the column at a position above the stationary phase, and a second pressure source fluidly connectable to the column at a position below the stationary phase, the first pressure source and the second pressure source having a first state which applies pressure to the column from the first pressure source, and a second state which applies pressure to the column from the second pressure source; and an actuator for switching the first pressure source and the second pressure source between the first state and the second state.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings, in which.

DETAILED DESCRIPTION

I. Definitions

Figure 1:
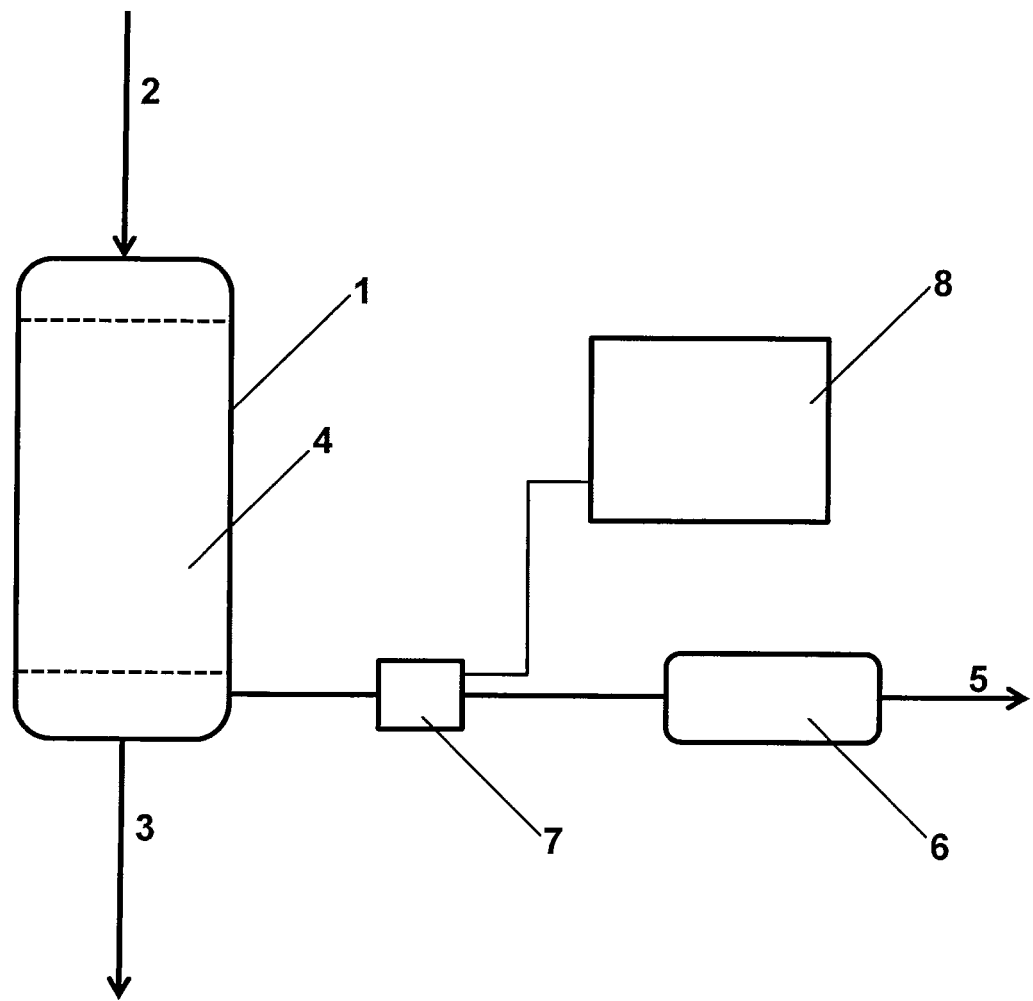
FIG. 1 is a schematic diagram of a method according to an embodiment of the present disclosure.

Unless otherwise indicated, the definitions and embodiments described in this and other sections are intended to be applicable to all embodiments and aspects of the disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "time-pulsed pressure differential" as used herein refers to the application of different pressures, including both positive and negative pressures, during chromatography, in a timed fashion, for example an alternating timed fashion.

The term "sample" as used herein refers to a mixture comprising, consisting essentially of or consisting of two or more sample components to be separated in a method or apparatus of the present disclosure.

The term "sample components" as used herein refers to chemically distinct constituents of the sample.

The term "stationary phase" as used herein refers to a phase that remains in a column used for chromatographic separation. The choice of a suitable stationary phase for a particular sample will depend, for example on the chemical nature of the sample components to be separated such as but not limited to polarity, acidity/basicity, whether the sample components are ionic species or neutral compounds and/or whether or not a sample component is acid sensitive. The selection of a suitable stationary phase for a particular sample can be made by a person skilled in the art. For example, silica gel ($SiO_2$) and alumina ($Al_2O_3$) are two common stationary phases used in chromatographic separation. Silica gel can be, for example normal phase silica (i.e. silica having terminal silanol groups), reversed phase silica (i.e. silica wherein terminal silanol groups have been end-capped with a non-polar group such as octadecyl, octyl or phenyl) or functionalized silica (i.e. silica wherein terminal silanol groups have been end-capped with an organic functional group comprising, for example an —$NH_2$ group or a cyano group). Alumina can be, for example acidic, neutral or basic. In an embodiment of the present disclosure, the stationary phase comprises a magnesium silicate such as Florisil™, a cross-linked dextran gel such as Sephadex™ a reversed-phase silica gel or normal phase silica gel. In another embodiment of the present disclosure, the stationary phase comprises normal phase silica gel.

The term "mobile phase" as used herein refers to a fluid which passes through and/or along the stationary phase. In an embodiment, the mobile phase is a liquid mobile phase. The choice of a suitable mobile phase for a particular sample will depend, for example on the chemical nature of the sample components and/or the nature of the stationary phase. The selection of a suitable mobile phase for a particular sample can be made by a person skilled in the art. The mobile phase comprises, consists essentially of or consists of a single solvent, or it comprises, consists essentially of or consists of two or more solvents. If the mobile phase comprises, consists essentially or consists of at least two solvents, either "gradient elution" or "isocratic elution" can be used during a chromatographic separation.

The term "isocratic elution of the liquid mobile phase" as used herein with reference to a method for chromatographic separation, refers to maintaining the composition of the liquid mobile phase substantially constant throughout the method.

The term "gradient elution of the liquid mobile phase" as used herein with reference to a method for chromatographic separation, refers to continuously changing the composition of the liquid mobile phase from one composition to another, for example toward conditions favoring dissociation of a sample component from a stationary phase used in the method. In an embodiment of the present disclosure, the composition of the liquid mobile phase is changed during operation of the method in about 5% v/v increments from a composition comprising about 100% of a first solvent to a composition comprising about 100% of a second solvent.

The term "sample rich liquid mobile phase" as used herein refers to a mobile phase in which the sample components that are soluble in the mobile phase are dissolved. A person skilled in the art would readily understand that the chemical composition of the sample rich liquid mobile phase as it elutes from a column used for a chromatographic separation of two or more sample components may change over time as a function of a difference in the retention of each of the two or more sample components in the column.

The expression "until separation of the two or more sample components is at least substantially complete" as used herein with reference to a method for chromatographic separation of two or more sample components means that each of the two or more sample components has eluted from a stationary phase of a column used for the chromatographic separation, and the peak separation between each of the two or more eluting sample components is at least about 90%, about 91%, about 92%, about 93%, about 94%, about 95%, about 96%, about 97%, about 98%, about 99%, about 99.5%, or about 100%.

The term "$R_f$" as used herein refers to "retention factor". A retention factor for a particular solute and mobile phase can be calculated by dividing the distance traveled by the solute on a planar or thin layer chromatograph by the distance traveled by the mobile phase on the planar or thin layer chromatograph.

The term "actuator" as used herein refers to a mechanism for controlling a system, in particular for switching the system between a first state and a second state, for example on/off states.

The term "EtOAc" as used herein refers to ethyl acetate:

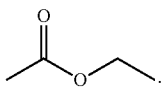

The term "Acet" as used herein refers to acetanilide:

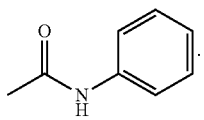

The term "Nmet" as used herein refers to N-methyl p-toluenesulfonamide:

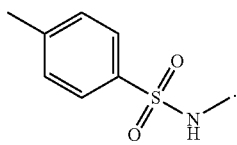

II. Methods

A comparison in separation efficiency between known chromatographic methods and the time-pulsed methods of the present disclosure (driven by either negative or positive pressure) has been made. The methods are compared in terms of adsorbent amounts, solvent volumes, separation efficiency of a binary mixture, and total time required for separation. It was found that the alternating pressure or pulsed methods are superior on all counts to the known ones.

Figure 2:
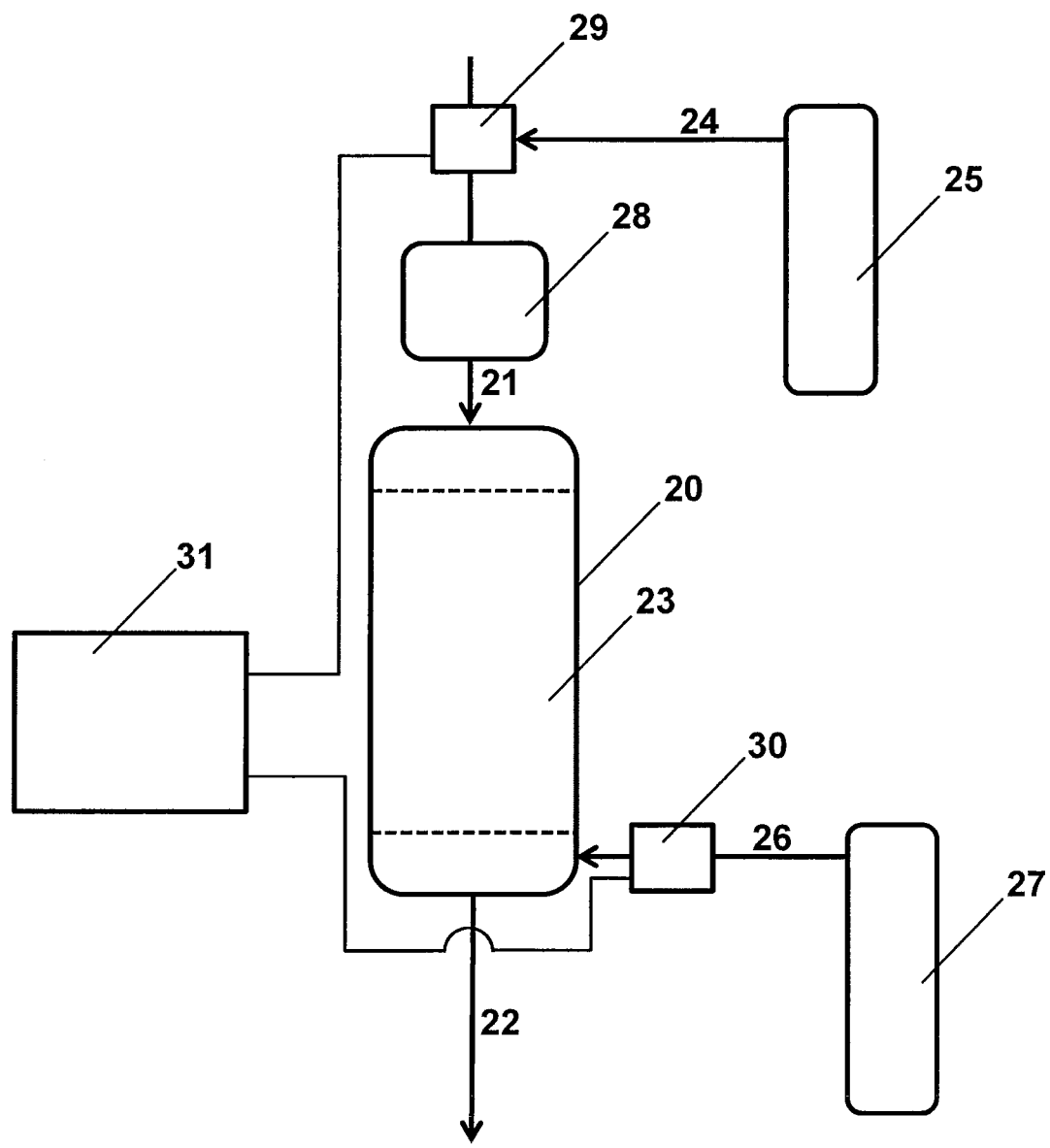
FIG. 2 is a schematic diagram of a method according to another embodiment of the present disclosure.

Exemplary flow diagrams for the methods of the present disclosure are shown in FIGS. 1 and 2. The methods exemplified therein are methods for chromatographic separation of two or more sample components. Referring to FIGS. 1 and 2, in the methods exemplified therein, a sample (not shown) is introduced into a column (1, 20). The column (1, 20) has at least one inlet (not shown) for receiving a liquid mobile phase (2, 21) at a first end of the column (1, 20), at least one outlet (not shown) for eluting a sample rich liquid mobile phase (3, 22) at a second end of the column (1, 20) and a stationary phase (4, 23) housed between the at least one inlet and the at least one outlet. The sample comprises, consists essentially of or consists of the two or more sample components to be chromatographically separated, and is introduced into the first end of the column (1, 20) so that it is in contact with the stationary phase (4, 23). The sample and the stationary phase (4, 23) are then contacted with the liquid mobile phase (2, 21) to obtain the sample rich liquid mobile phase (3, 22) while at least one time-pulsed pressure differential is applied to the column (1, 20).

Accordingly, the present disclosure includes a method for chromatographic separation of two or more sample components comprising: applying at least one time-pulsed pressure differential to a column during chromatographic separation of two or more sample components.

In an embodiment, the method for chromatographic separation of two or more sample components comprises:
 a) introducing a sample into a column, the column having at least one inlet for receiving a liquid mobile phase at a first end of the column, at least one outlet for eluting a sample rich liquid mobile phase at a second end of the column, a stationary phase housed between the at least one inlet and the at least one outlet, the sample comprising the two or more sample components and being introduced into the first end of the column so that it is in contact with the stationary phase; and
 b) contacting the sample and the stationary phase with the liquid mobile phase and obtaining the sample rich liquid mobile phase while applying at least one time-pulsed pressure differential to the column.

The method used for applying the at least one time-pulsed pressure differential to the column can vary. For example, in the embodiment exemplified in FIG. 1, applying the time-pulsed pressure differential to the column 1 comprises applying a vacuum 5 to the column 1 using a vacuum source 6 coupled to the column 1 at a position below the stationary phase 4, stopping the vacuum 5 applied to the column 1, and reapplying the vacuum 5 applied to the column 1. Optionally, the method further comprises repeating the stopping the vacuum 5 applied to the column 1 and reapplying the vacuum 5 applied to the column 1 until separation of the two or more sample components is at least substantially complete.

Accordingly, in an embodiment of the present disclosure, applying the time-pulsed pressure differential to the column comprises:
 a) applying a vacuum to the column using a vacuum source coupled to the column at a position below the stationary phase;
 b) stopping the vacuum applied to the column;
 c) reapplying the vacuum to the column; and
 d) optionally repeating b)-c) until separation of the two or more sample components is at least substantially complete.

The vacuum source 6 can be coupled to the column 1 through various means so long as it is coupled to the column 1 at a position below the stationary phase 4 and so long as it applies vacuum 5 to the column 1. For example, the vacuum source 6 is coupled to the at least one outlet for eluting the sample rich liquid mobile phase 3. Alternatively, the vacuum source 6 is coupled to column 1 itself at a position below the stationary phase 4.

In an embodiment, the vacuum source 6 has a first state which applies the vacuum 5 to the column 1, and a second state which stops application of the vacuum 5 to the column 1. In an embodiment, an actuator is used to switch the vacuum source 6 between the first state and the second state.

For example, the first state is the vacuum source 6 in an "on" state, the second state is the vacuum source 6 in an "off" state, and the actuator is an "on/off" mechanism such as an on/off switch. Alternatively, a pressure releaser 7 as shown in FIG. 1 such as a pressure release valve is optionally present between vacuum source 6 and column 1. In this embodiment, switching the vacuum source 6 between the first state and the second state comprises using the actuator to control the closing and opening of the pressure releaser 7 such as a pressure release valve.

The vacuum source 6 referred to in FIG. 1 comprises, for example a vacuum pump or a water aspirator. In an embodiment, the vacuum source 6 comprises a dry vacuum pump; i.e. a vacuum pump that does not use an auxiliary liquid such as oil. In another embodiment, the vacuum source 6 comprises a portable dry vacuum pump, for example a small dry vacuum pump.

In an embodiment, the vacuum source 6 applies a vacuum 5 of about 450 mm Hg to about 650 mm Hg. In another embodiment, the vacuum source 6 applies a vacuum of about 650 mm Hg.

The particular intervals at which the vacuum source 6 is switched between the first state and the second state depends, for example on the two or more sample components being separated as well as the particular apparatus used in the method and can be determined by a person skilled in the art. For example, the vacuum 5 applied to the column 1 is stopped for a time so that a shock wave travelling back up the column 1 is visible, and the vacuum 5 is reapplied to the column 1 once the pressure equilibrates in the column 1.

Accordingly, in an embodiment, the applying a vacuum 5 to the column 1 and/or reapplying the vacuum 5 to the column 1 are run for a time of about 3 seconds to about 10 seconds or about 5 seconds, and the stopping the vacuum 5 applied to the column 1 is run for about 5 seconds to about 15 seconds, about 5 seconds or about 10 seconds. The time for applying the vacuum 5 to the column and/or reapplying the vacuum 5 to the column varies, for example based on the fraction size, the porosity of the stationary phase 4 such as silica gel, the porosity of a frit (if present) in the column 1 (not shown), the diameter of column 1, the sample loading and/or the strength of the vacuum 5 and can be determined by a person skilled in the art. The time for stopping the vacuum 5 applied to the column 1 varies, for example based on the rate a vessel, such as a tube for fraction collection, is changed, and can be determined by a person skilled in the art. In an embodiment of the present disclosure, the applying a vacuum 5 to the column 1 and/or reapplying the vacuum 5 to the column 1 are each run for a time that does not substantially vary over the operation of the method. Fixed timing, for example, gives a straightforward operation. In another embodiment, the applying a vacuum 5 to the column 1 and/or reapplying the vacuum 5 to the column 1 are run for a time that varies over the operation of the method. For example, the time the vacuum 5 is reapplied to the column 1 is made shorter by about ⅓ after the collection/chromatography is at least half finished and the stationary phase 4, such as silica gel, is saturated with mobile phase so as not to compromise the size of fraction collected during operation of the method.

In the embodiment exemplified in FIG. 2, applying the time-pulsed pressure differential to the column 20 comprises applying a first pressure 24 to the column 20 using a first pressure source 25 coupled to the column 20 at a position above the stationary phase 23. The first pressure 24 applied to the column 20 is then stopped, and a second pressure 26 is applied to the column 20 using a second pressure source 27 coupled to the column 20 at a position below the stationary phase 23. The second pressure 26 applied to the column 20 is then stopped, and the first pressure 24 reapplied to the column 20. In an embodiment of the present disclosure, the applying the first pressure 24 to the column 20 using the first pressure source 25 coupled to the column 20 at a position above the stationary phase 23, stopping the first pressure 24 applied to the column 20 and applying the second pressure 26 to the column 20 using the second pressure source 27 coupled to the column 20 at a position below the stationary phase 23 and stopping the second pressure 26 applied to the column 20 and reapplying the first pressure 24 applied to the column 20 are optionally repeated until the separation of the two or more sample components is at least substantially complete.

Accordingly, in another embodiment of the present disclosure, applying the time-pulsed pressure differential to the column comprises:
a) applying a first pressure to the column using a first pressure source coupled to the column at a position above the stationary phase;
b) stopping the first pressure applied to the column and applying a second pressure to the column using a second pressure source coupled to the column at a position below the stationary phase;
c) stopping the second pressure applied to the column and reapplying the first pressure applied to the column; and
d) optionally repeating b)-c) until separation of the two or more sample components is at least substantially complete.

In this embodiment, the first pressure source 25 and the second pressure source 27 are coupled to the column 20 through various means so long as the first pressure source 25 is coupled to the column 20 at a position above the stationary phase 23, the second pressure source 27 is coupled to the column 20 at a position below the stationary phase 23, and so long as the first pressure source 25 can apply a first pressure 24 to the column 20 and the second pressure source 27 can apply a second pressure 26 to the column 20. For example, the first pressure source 25 is coupled to the at least one inlet for receiving a liquid mobile phase 21. Alternatively, the first pressure source 25 is coupled to the column 20 itself at a position above the stationary phase 23. In another embodiment, a solvent reservoir 28 as shown in FIG. 2 is optionally present between the first pressure source 25 and the column 20, and the first pressure source 25 is coupled at a position above the solvent reservoir 28. In a further embodiment, the second pressure source 27 is coupled to the at least one outlet for eluting the sample rich liquid mobile phase 22. Alternatively, the second pressure source 27 is coupled to the column 20 itself at a position below the stationary phase 23.

In an embodiment, the first pressure source 25 and the second pressure source 27 have a first state which applies pressure to the column 20 from the first pressure source 25 and a second state which applies pressure to the column 20 from the second pressure source 27. In an embodiment, an actuator is used to switch the first pressure source 25 and the second pressure source 27 between the first state and the second state.

For example, the first state is the first pressure source 25 in an "on" state and the second pressure source 27 in an "off" state, the second state is the first pressure source 25 in an "off" state and the second pressure source 27 in an "on" state, and the actuator is an "on/off" mechanism such as a switch controlling the pressure sources. Alternatively, a first valve 29 as shown in FIG. 2 is optionally present between the first pressure source 25 and the column 20, and/or a second valve 30 is optionally present between the second pressure source 27 and the column 20. In this embodiment, switching the first pressure source 25 and the second pressure source 27 between the first state and the second state comprises using the actuator to control the closing and opening of the valves.

The first pressure source 25 and/or the second pressure source 27 comprise, for example a source of pressurized gas. In an embodiment, each of the first pressure source 25 and the second pressure source 27 comprise a source of pressurized inert gas. In another embodiment, the source of inert gas is nitrogen or argon. In an embodiment, the pressurized inert gas is nitrogen. Standard tanks comprising pressurized inert gases such as compressed nitrogen gas are available from commercial sources, for example Praxair.

In another embodiment, the first pressure source 25 applies a first pressure 24 of about 5 psi to about 10 psi or about 8 psi. In another embodiment, the second pressure source 27 applies a second pressure 26 of about 5 psi to about 10 psi or about 8 psi. The selection of a first pressure 24 and second pressure 26 varies, for example based on the fraction size, the porosity of the stationary phase 23 such as silica gel, the porosity of a frit(s) used in the column 20 (not shown), the diameter of the column 20 and/or the sample loading and can be made by a person skilled in the art.

The particular intervals at which the first pressure source 25 and the second pressure source 27 are switched between the first state and the second state will depend, for example on the two or more sample components being separated as well as the particular apparatus used in the method and can be determined by a person skilled in the art.

Accordingly, in an embodiment the applying a first pressure 24 to the column 20 using a first pressure source 25 and/or stopping the second pressure 26 applied to the column 20 and reapplying the first pressure 24 to the column 20 are run for a time of about 5 seconds to about 15 seconds, about 5 seconds or about 10 seconds, and the stopping the first pressure 24 applied to the column 20 and applying a second pressure 26 to the column 20 is run for about 3 seconds to about 10 seconds, about 5 seconds or about 10 seconds. The selection of a time varies, for example, on the fraction size, the porosity of the stationary phase 23, such as silica gel, the porosity of a frit(s) (if present) in the column 20, the diameter of the column 20, the sample loading and the applied pressure and can be made by a person skilled in the art. In an embodiment, the time the first pressure 24 applied to the column 20 is stopped and the second pressure 26 is applied to the column 20 is shorter than the time the first pressure 24 is applied to the column 20 using a first pressure source 25 and/or the second pressure 26 applied to the column 20 is stopped and the first pressure 24 to the column 20 is reapplied. In another embodiment, the first pressure 24 applied to the column 20 is stopped and the second pressure 26 is applied to the column 20 for a time that is about ½ to about ⅔ of the time the first pressure 24 is applied to the column 20 using a first pressure source 25 and/or the second pressure 26 applied to the column 20 is stopped and the first pressure 24 to the column 20 is reapplied.

In an embodiment, applying the time-pulsed pressure differential to the column (1, 20) is manually controlled. For example, during operation of the method exemplified in FIG. 1, a human subject manually actuates an actuator, for example an on/off mechanism for the vacuum source 6 or an actuator controlling the opening and closing of pressure releaser 7 so that the vacuum source 6 is switched between the first state and the second state at particular intervals. For example, during operation of the method exemplified in FIG. 2, a human subject manually actuates an actuator, for example an on/off mechanism for the first pressure source 25 and the second pressure source 27 or an actuator controlling the opening and closing of the first valve 29 and the second valve 30 so that the first pressure source 25 and the second pressure source 27 are switched between the first state and the second state at particular intervals.

In an embodiment, applying the time-pulsed pressure differential to the column (1, 20) is automatically controlled. In another embodiment, a programmable controller (8, 31) as shown in FIGS. 1 and 2 automatically controls applying the time-pulsed pressure differential to the column (1, 20). For example, in the embodiment exemplified in FIG. 1, the programmable controller 8 controls the pressure releaser 7 or the programmable controller 8 controls an actuator controlling the pressure releaser 7. For example, in the embodiment exemplified in FIG. 2, the programmable controller 31 controls the first valve 29 and the second valve 30 or the programmable controller controls an actuator controlling the first valve 29 and the second valve 30. It will be appreciated that there are other ways, within the knowledge of a person skilled in the art, of using a programmable controller (8, 31) to control applying the time-pulsed pressure differential to the column (1, 20). The selection of a suitable programmable controller (8, 31) can be made by a person skilled in the art. A programmable controller (8, 31) can be custom-made for a particular method or can be obtained from a commercial source. For example, Ace Glass catalogue no. 14033-10 (vacuum monitor and controller) is an example of a device for controlling pressure and/or vacuum.

In an embodiment, the method comprises isocratic elution of the liquid mobile phase (2, 21). In another embodiment, the method comprises gradient elution of the liquid mobile phase (2, 21). In another embodiment, the composition of the liquid mobile phase (2, 21) is changed during operation of the method in about 3% v/v to about 10% v/v increments or about 5% v/v increments from a composition comprising, consisting essentially of or consisting of about 100% of a first solvent to a composition comprising, consisting essentially of or consisting of about 100% of a second solvent.

In an embodiment, the sample is introduced into the first end of the column (1, 20) as a composition comprising the sample adsorbed to an adsorbent having the same constitution as the stationary phase (4, 23). For example, the composition is prepared by dissolving the sample to be separated in a suitable solvent. The suitable solvent is one in which the sample components are soluble. In an embodiment, dissolution is assisted by using sonication and/or heating. The solution comprising the sample and solvent is then contacted with the adsorbent under conditions to adsorb the sample to the adsorbent. In an embodiment, the ratio by weight of the sample:adsorbent is from about 0.5:1 to about 1:4. In another embodiment of the present disclosure, a neat sample, for example a sample comprising, consisting essentially of or consisting of two or more sample components that are solids is directly introduced into the first end of the column (1, 20). In another embodiment, the sample is introduced into the first end of the column (1, 20) as a solution comprising the sample dissolved in a minimum amount of the more polar solvent of a liquid mobile phase (2, 21) comprising two solvents.

In an embodiment, the method further comprises collecting one or more fractions of the sample rich liquid mobile phase (3, 22).

In an embodiment, the stationary phase comprises, consists essentially of or consists of silica gel. In another embodiment, about 30 g to about 42 g, or about 36 g of silica gel (dry weight) are used in the method for each about 2 g of sample to be separated. The amount of stationary phase (4, 23) used per amount of sample to be separated varies, for example, on the extent of the separation of the sample components on the stationary phase (4, 23) as exemplified by their respective $R_f$ values and/or the liquid mobile phase (2, 21) used and can be determined by a person skilled in the art. In a further embodiment, the weight ratio of silica gel to sample to be separated is about 50:1 to about 10:1, about 40:1 to about 15:1 or about 30:1 or about 20:1.

III. Apparatuses

Figure 3:
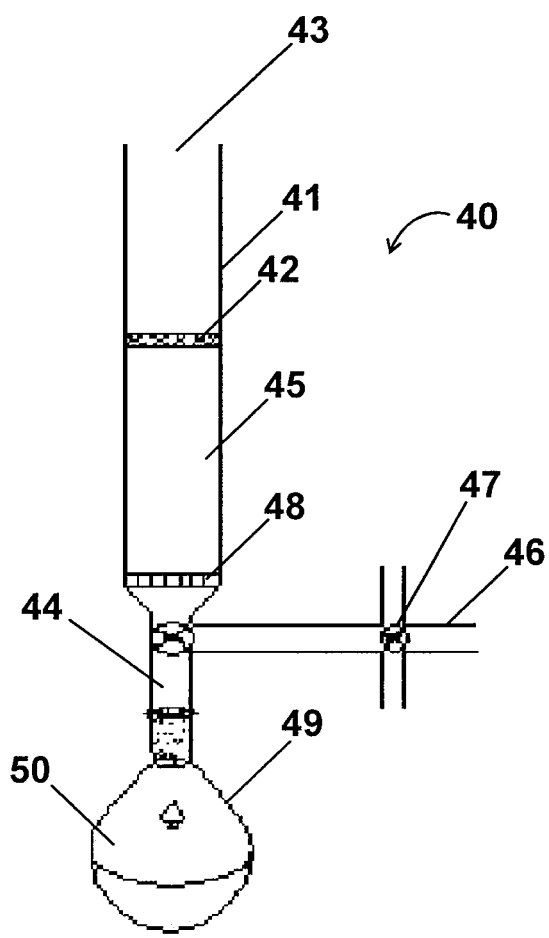
FIG. 3 is a partial front plan view of an apparatus according to an embodiment of the present disclosure.
Figure 4:
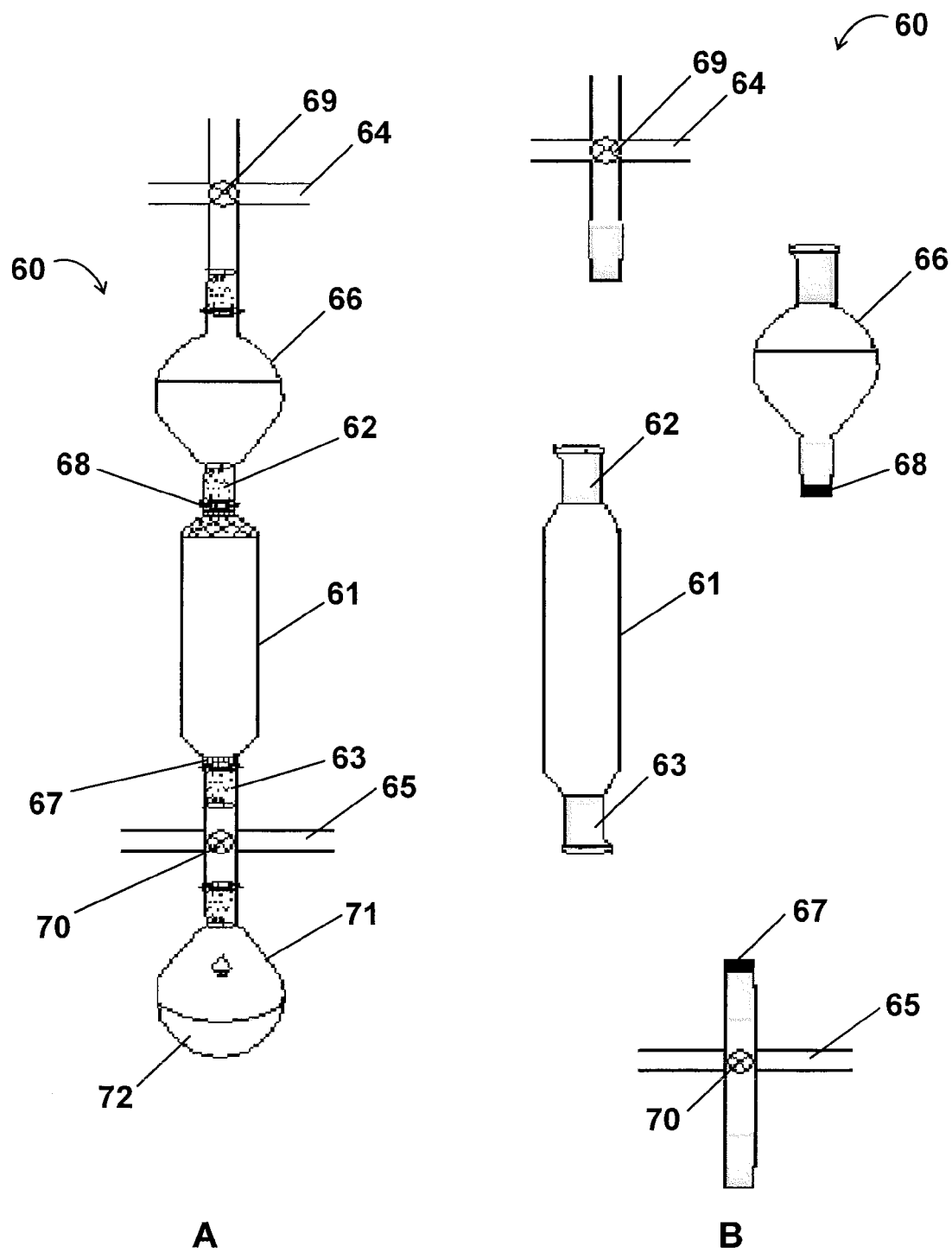
FIG. 4A is a partial front plan view of an apparatus according to another embodiment of the present disclosure.
FIG. 4B is an exploded partial front plan view of the apparatus shown in FIG. A4.

FIGS. 3, 4A and 4B show examples of apparatuses for time-pulsed chromatography. Referring to FIGS. 3, 4A and 4B, the apparatus (40, 60) comprises a column (41, 61) for separating a sample (42, not shown) comprising two or more sample components, the column having at least one inlet (43, 62), at least one outlet (44, 63), a stationary phase (45, not shown) positioned between the at least one inlet (43, 62) and the at least one outlet (44, 63), and a pump (not shown). The pump is configured to apply at least one time-pulsed pressure differential to the at least one inlet (43, 62) and/or the at least one outlet (44, 63) of the column (41, 61).

Accordingly, the present disclosure includes a chromatography apparatus comprising: a column having an inlet, an outlet and a pump, wherein the pump is configured to apply at least one time-pulsed pressure differential to the inlet and/or the outlet of the column.

In an embodiment, the apparatus for time-pulsed chromatography comprises:

a column for separating a sample comprising two or more sample components, the column having at least one inlet, at least one outlet, a stationary phase positioned between the at least one inlet and the at least one outlet; and a pump, wherein the pump is configured to apply at least one time-pulsed pressure differential to the at least one inlet and/or the at least one outlet of the column.

The configuration of the pump to apply the at least one time-pulsed pressure differential can vary. For example, in the embodiment exemplified in FIG. 3, the pump comprises a vacuum source (not shown) fluidly connectable to the column 41 at a position below the stationary phase 45 such as via connection 46. The vacuum source has a first state which applies a vacuum to the column 41 and a second state which stops application of the vacuum to the column 41. The pump further comprises an actuator (not shown) for switching the vacuum source between the first state and the second state.

Accordingly, in an embodiment of the present disclosure, the pump comprises: a vacuum source fluidly connectable to the column at a position below the stationary phase, the vacuum source having a first state which applies a vacuum to the column and a second state which stops application of the vacuum to the column; and an actuator for switching the vacuum source between the first state and the second state.

In another embodiment, the apparatus 40 further comprises a pressure releaser 47 such as a pressure release valve between the column 41 and the vacuum source (not shown), and switching the vacuum source between the first state and the second state comprises closing and opening the pressure releaser 47 such as a pressure release valve.

In an embodiment, connection 46 comprises a vacuum-safe glass manifold such as a pressure manifold available through Ace Glass (catalog no. 6448) having a vacuum gauge, for example an about 0 to about 60 psi pressure gauge comprising stainless steel internals; a vacuum relief valve, for example an about 0 to about 50 psi adjustable relief valve; and optionally, as a safety feature, a rupture disc, for example an over-pressure safety rupture disc.

Referring to FIGS. 4A and 4B, in the embodiment exemplified therein, the pump comprises a first pressure source (not shown) fluidly connectable to the column 61 at a position above the stationary phase (not shown) such as via first connection 64, and a second pressure source (not shown) fluidly connectable to the column 61 at a position below the stationary phase such as via second connection 65. In an embodiment, the first connection 64 and the second connection 65 comprise thick-walled glass assemblies having an internal three-way valve such as a stopcock therein that can, for example be switched between being fluidly connected to a pressure source and allowing for mobile phase flow therethrough. The first pressure source and the second pressure source have a first state which applies pressure to the column 61 from the first pressure source and a second state which applies pressure to the column 61 from the second pressure source. The pump further comprises an actuator (not shown) for switching the first pressure source and the second pressure source between the first state and the second state.

Accordingly, in an embodiment, the pump comprises: a first pressure source fluidly connectable to the column at a position above the stationary phase, and a second pressure source fluidly connectable to the column at a position below the stationary phase, the first pressure source and the second pressure source having a first state which applies pressure to the column from the first pressure source, and a second state which applies pressure to the column from the second pressure source; and an actuator for switching the first pressure source and the second pressure source between the first state and the second state.

In another embodiment, the apparatus 60 further comprises a solvent reservoir 66 as shown in FIGS. 4A and 4B positioned between the first pressure source (not shown) and the at least one inlet 62.

In an embodiment, the first pressure source and/or the second pressure source comprises a source of pressurized gas. In an embodiment of the present disclosure, each of the first pressure source and the second pressure source comprises a source of pressurized inert gas. In another embodiment, the inert gas is nitrogen or argon. It is an embodiment that the inert gas is nitrogen. Standard tanks comprising pressurized inert gases such as compressed nitrogen gas are available from commercial sources, for example Praxair.

In a further embodiment, referring to FIGS. 3, 4A and 4B, the apparatus (40, 60) further comprises a first frit (48, 67) spanning the column (41, 61) at a position between the at least one inlet (43, 62) and the at least one outlet (44, 63). The first frit (48, 67) has at least one aperture such as a pore sized to allow a liquid and/or a gas to pass through and to allow the stationary phase (45, not shown) to be retained in the column (41, 61). In an embodiment, the first frit is a frit for coarse filtration applications, for example a standard glass frit having a pore size of about 70 microns to about 100 microns.

In another embodiment, the apparatus exemplified in FIGS. 4A and 4B further comprises a second frit 68 spanning the column 61 at a position between the solvent reservoir 66 and the stationary phase (not shown). The second frit 68 has at least one aperture such as a pore sized to allow a liquid and/or a gas to pass through and to allow the stationary phase to be retained in the column 61. In an embodiment, the second frit is a frit for coarse filtration applications, for example a standard glass frit having a pore size of about 70 microns to about 100 microns.

In another embodiment, the apparatus further comprises a vessel (49, 71) as shown in FIGS. 3 and 4A for collecting one or more fractions of a sample rich mobile phase (50, 72) that has eluted from the apparatus.

In an embodiment of the present disclosure, the actuator is manually controlled. For example, if the actuator is an "on/off" mechanism such an on/off switch for the pump, a human subject manually switches the on/off switch between an "on" position and an "off" position at a particular interval. For example, if the actuator controls the closing and opening of pressure releaser 47 shown in FIG. 3 such as a pressure release valve, a human subject manually actuates the actuator to switch the pressure releaser 47 such as a pressure release valve between a closed position and an open position so that the vacuum source is switched between the first state and the second state at a particular interval. For example, if the actuator controls the closing and opening of first valve 69 and second valve 70 referred to in FIGS. 4A and 4B, a human subject manually actuates the actuator to switch the first valve 69 and the second valve 70 alternately between a closed and an open position so that the first pressure source and the second pressure source are switched between the first state and the second state at a particular interval.

In another embodiment, the actuator is automatically controlled. In an embodiment, a programmable controller (not shown) automatically controls the actuator. The selection of a suitable programmable controller can be made by a person skilled in the art. A programmable controller can be custom-made for a particular apparatus or can be obtained from a commercial source. For example, Ace Glass catalogue no. 14033-10 (vacuum monitor and controller) is an example of a device for controlling pressure and/or vacuum. For example, a programmable controller can actuate the actuators that the human subject actuated in any of the above embodiments.

The following non-limiting examples are illustrative of the present disclosure:

EXAMPLE

I. Methods:
(a) Time-pulsed Vacuum Chromatography

The column (for example, a column having a length of 10 cm and a diameter of 3 cm) was packed dry and the mixture of compounds was pre-adsorbed on silica and the dry silica then placed on top of the column bed. The less polar component of the solvent system was used to begin the elution under vacuum for gradient elution (~600-650 mm Hg), and a 1:1 mixture of hexanes and EtOAc was used for isocratic elution. The vacuum was interrupted at specified intervals (usually 5 or 10 seconds of flow). The shock wave travelling back up the column was visible and after the pressure equilibrated the vacuum was applied again. Fraction volume depends on the scale of separation. Details of the separation protocols and summaries of results are listed in Tables 1 to 17.

(b) Time-pulsed Alternating Pressure Chromatography.

The column was packed dry and the mixture of compounds was pre-adsorbed on silica and the dry silica placed on top of the column bed. A 1:1 mixture of hexanes and EtOAc was used for isocratic elution under 8 psi nitrogen gas pressure. Nitrogen gas pressure was applied in opposite directions (FIG. 4) through first and second connections 64 and 65 at specified intervals (usually 5 or 10 seconds of flow). Bubbling is visible once the pressure is applied from the bottom of the column. Fraction volume was based on initial results with time-pulsed vacuum chromatography (Details of the separation protocols and summaries of results are listed in the Tables 1 through 17).

II. Results and Discussion

A comparison was made in the studies of the present disclosure between conventional gravity chromatography, flash column chromatography, and suction filtration chromatography with timed interruptions of pressure. The general procedure is described in the methods section, above. The results are summarized in Table 18 with additional details in Tables 1 to 17.

In each case, 2 grams of a mixture of acetanilide and N-methyl p-toluenesulfonamide (1 gram each) ($R_f$=0.42 and 0.64, respectively; hexane/EtOAc, 1:1 elution solvent) was used.

The results clearly indicate that the time-pulsed interruption of pressure has a beneficial effect on the separation. In dry column vacuum suction[4] or vacuum liquid chromatography[5] effort was made NOT to interrupt the vacuum during fraction collection. In the case of time-pulsed vacuum filtration the intentional interruption of vacuum sends a pressure wave backwards through the separation bed. Thus the components of the mixture travel down an active surface for time=$t_1$ and distance=$d_1$ then, as the pressure is interrupted, travel backwards over a partially saturated surface, modified by the presence of the adsorbed component, for time=$t_2$ and distance=$d_2$. The net effect that the pulsing has on the separation is that the components spend more time on an "apparently" longer bed of adsorbent (time, $T=t_1+2t_2$ and distance, $D=d_1+2d_2$). The separation process is therefore the function of the initial negative pressure, the reverse pressure gradient, the time regime of pulsing and the change in the characteristics of the stationary phase caused by adsorption of the solute. See the section entitled "Discussion of principles involved" for a discussion of the non-limiting proposed theory.

From the data in Table 18 it is clear that the time-pulsed vacuum filtration method is useful in comparison to the other forms of chromatography studied in terms of adsorbent loading, time of separation, and the volume of solvent used—all of which parameters in the methods of the present disclosure are more effective than those from the two standard methods used for comparison.

Repetition of the original vacuum dry column method published in 2001[4] produced results that were most similar to the pulsed vacuum protocol except that it required ~20% more solvent [Silica=36 g; No. of fractions=20; Solvent 600 mL; Time 14 min]. This observation makes sense as the vacuum had to be interrupted in the original procedure for fractions to be collected. Some advantages of the pulsed vacuum protocol over the dry column vacuum chromatography include the adjustability of the time regime of the pulses and the lower volumes of solvent used, especially at larger scales.

In addition, a method of pressure-pulsed chromatography has been designed that combines the principles of flash chromatography with the time-pulsed vacuum suction filtration. The pressure is applied in one direction for time $t_1$, interrupted, and reapplied in the opposite direction for time=$t_2$. The principle is similar to that described for pulsed vacuum chromatography except that positive pressure is employed to move the mixture through the adsorbent bed in an oscillating manner. In the trials summarized in Table 14, about 30 grams of silica gel was used in a shorter column. The results from these trials indicated that a longer column was needed to accommodate the amount of silica gel useful to achieve a good resolution (about 40 grams). The results are shown in the last two columns in Table 17 for comparison with the vacuum pulsed protocol.

III. Discussion of Principles Involved

The separation of a mixture is a function of the free energy of adsorption of the components and, and, in accordance with the Van Deemter equation, $$H = A + \frac{B}{u} + Cu$$

is also a function of velocity of flow over the adsorptive surface, where H=theoretical plate height and u=velocity of the mobile phase. The coefficients A, B and C represent, respectively, tortuosity, longitudinal diffusion and mass transfer coefficient between mobile and stationary phases. It is the C factor, the mass transfer coefficient, that is most significant in this application. In time-pulsed chromatography, the additional parameters that need to be considered are the pressure gradients and time.

Consideration of equilibrium thermodynamics allows an equation to be developed that relates pressure and the distribution coefficient for the solute between the mobile and stationary phases.[6] The term $\Delta G_{dist}$ is the Gibbs free energy of binding of the solute to the stationary phase, $K_{dist}$ is the distribution coefficient for the solute, $\Delta V$ is a measure of the pressure-induced change in the partial molar volume and $\Delta n$ is the change in coefficients of solute between the mobile and stationary phases; $\kappa_s$ is the isothermal compressibility of the solvent:

$$\left(\frac{\partial G_{distr}}{\partial P}\right)_T = -RT\left(\frac{\partial K_{distr}}{\partial P}\right)_T + \Delta nRT\kappa_s = \Delta V$$

The above equation can be developed to show the relationship between pressure and the selectivity factor α:

$$-RT\frac{\Delta \ln \alpha}{\Delta P} = \Delta V$$

This effect will be small at the modest pressures used in the methods of the present disclosure. the term $\Delta V/RT$ approaches zero, leaving the relationship:

$$\left(\frac{\partial \ln K_{dist}}{\partial P}\right)_T = \Delta nRT\kappa_s$$

The effect of the reversal of the direction has a twofold effect: one is the virtual lengthening of the column, as outlined above; the second would be that the reversal of the flow would have the effect of reconcentrating, or focussing the solutes on the stationary phase that is partially covered with the solute.

Stationary phases with adsorbed solute would be expected to have a greater affinity, and thereby would increase the distribution coefficient. The consequence of this change and reconcentration would be that the adsorption profile would be sharpened, and the width of the peak narrowed, which would, in turn, affect the number of theoretical plates, as can be seen from the equation below, where N=number of theoretical plates, $t_R$=retention time, and w=peak width.

$$N = 16\left(\frac{t_R}{w}\right)^2$$

Resolution (R) between two eluting peaks is a function of the number of theoretical plates (N), the selectivity coefficient (α), and the retention factor ($k_B'$) of the later-eluting peak, as shown in the equation below.

$$R = \frac{\sqrt{N}}{4}\left(\frac{\alpha - 1}{\alpha}\right)\left(\frac{k_B'}{1 + k_B'}\right)$$

In addition, the retention factor depends upon the time taken by the solvent and the solute to pass through the column, as shown in the equation below.

$$k' = \frac{t_R - t_M}{t_M}$$

These times will depend upon the programming of the pressure regime, as described above and will be consistent with the notional longer bed.

The other important factors to be taken into consideration, and that have an impact upon the peak width, are the changes in the retention factors for the eluents as they undergo reversal of flow direction. This phenomenon is described by Poole in terms of Secondary Chemical Equilibria.[7] Although it might seem that the reversal of flow will merely remix the components, in fact, the change in distribution coefficients, or retention factors, as mentioned above, will, in fact, be altered three times at each reversal event:

1. The solute passes down the column with no adsorbed solute, $k_1$

2. At the first reversal, the solute in the mobile phase will be more strongly retained on the stationary phase since the stationary phase that partially saturates the surface. For this situation, $k_2$ will be greater than $k_1$ 3. The second reversal returns the solute over the stationary phase that has adsorbed even more of the solute, thereby increasing further, the value of the retention factor, $k_3$ Once the third step is achieved, the process can begin again, resulting in further sharpening of the elution profile.

Thus, the temporarily increased retention factor of the column, at the point where the solute can be more strongly adsorbed, results in the focusing, alluded to above. From the equations above, it will be clear that reducing the peak width will result in a greater number of theoretical plates, which in turn, will mean a greater resolution, since resolution is proportional to the square root of the number of theoretical plates.

Implications of this improved resolution include that i) satisfactory resolution of closely-eluting solutes may be achieved with a shorter column bed; ii) following from i), smaller volumes of eluting solvent may be required; iii) a smaller number of fractions may be needed to achieve functional separation of solutes and iv) separations may be achieved in a shorter time-frame.

IV. Conclusions

The studies of the present disclosure have demonstrated that time-pulsed or alternating pressure chromatography provides separations that are more effective than those acquired by known methods. The vacuum time-pulsed method as well as the alternating pressure method both use less solvent, less adsorbent, take less time to complete and provide comparable or better separation of standard binary mixtures compared with either gravity or flash column chromatography. These improvements are useful for applications at larger scales where the amount of adsorbent and the volume of solvent used are substantial and contribute to the increased costs of separation. With the use of the time-pulsed method large amounts of mixtures with $\Delta R_F = \sim 0.1$ have been routinely separated using a ratio of silica to compounds of ~20:1 (as compared to ~100:1 for conventional methods). It is especially useful for repetition of separation protocols with the same mixtures (as is often the case in projects dealing with total synthesis) where the first experiment is used as a trial run to determine more optimal conditions with regard to the regime of time-pulse and fraction collection.

In addition, both the time-pulsed vacuum method and the alternating pressure method are expected to be amenable to computer interface driven automation for the purpose of precise timing, variable vacuum and pressure adjustments, monitoring of separation and fraction collection. Also included in the present application is instrumentation that allows quantitative control of the experimental parameters in these separations.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

[1] Touchstone, Joseph C., "History of Chromatography". *Journal of Liquid Chromatography* 1993, 16:8, 1647-1665.
[2] Ettre, L. S., "The Predawn of Paper Chromatography". *Chromatographia* 2001, 54, 409-414.
[3] Still, W. C.; Kahn, M.; Mitra, A. *J. Org. Chem.* 1978, 43, 2923-2925.
[4] Pedersen, D. S.; Rosenbohm, C. *Synthesis* 2001, 2431.
[5] Targett, N. M.; Kilcoyne, J. P.; Green, B. *J. Org. Chem.* 1979, 44, 4962.
[6] Ringo, M. C.; Evans, C. E. *J. Microcolumn Separations* 1998, 10, 647-652.
[7] Poole, C. F. "The Essence of Chromatography", Elsevier Press, 2003, pp 315-316.

TABLE 1

Parameters that are Constant for all of the Flash and Gravity Column Chromatography Runs

| | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min. |
| Amount of Silica | 150 g |
| Volume of each fraction collected | 30 mL |
| Isocratic elution | 1:1 hexanes/EtOAc |

TABLE 2

Results for Flash Column Chromatography

| Trial 1 | |
|---|---|
| Total time for fraction collection | 39 min |
| Number of fractions | 35 |
| Elution volume (weight) of Acet | 630 mL (980 mg) |
| Elution volume (weight) of Nmet | 210 mL (950 mg) |
| Total volume of eluent | 1050 mL |
| Trial 2 | |
| Total time for fraction collection | 37 min |
| Number of fractions | 36 |
| Elution volume (weight) of Acet | 660 mL (990 mg) |
| Elution volume (weight) of Nmet | 240 mL (970 mg) |
| Total volume of eluent | 1080 mL |

TABLE 3

Results for Gravity Column Chromatography

| Trial 1 | |
|---|---|
| Total time for fraction collection | 75 min |
| Number of fractions | 40 |
| Elution volume of (weight) Acet | 575 mL (970 mg) |
| Elution volume of (weight) Nmet | 200 mL (965 mg) |
| Total volume of eluent | 1200 mL |
| Trial 2 | |
| Total time for fraction collection | 72 min |
| Number of fractions | 36 |
| Elution volume of (weight) Acet | 540 mL (990 mg) |
| Elution volume of(weight) Nmet | 180 mL (950 mg) |
| Total volume of eluent | 1080 mL |

TABLE 4

Parameters that are Constant for all of the Pulsed Suction Column Chromatography Runs

| | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Vacuum strength | 650 torr |
| Isocratic elution | 1:1 hexanes/EtOAc |

TABLE 5

Results for Pulsed Suction Column
Chromatography (pulse = 5 sec)

| Trial 1 | |
|---|---|
| Total time for fraction collection | 16 min |
| Number of fractions | 21 |
| Elution volume (weight) of Nmet | 75 mL (950 mg) |
| Elution volume (weight) of Acet | 225 mL (970 mg) |
| Total volume of eluent | 525 mL |
| Trial 2 | |
| Total time for fraction collection | 12 min |
| Number of fractions | 20 |
| Elution volume (weight) of Nmet | 75 mL (980 mg) |
| Elution volume (weight) of Acet | 225 mL (980 mg) |
| Total volume of eluent | 500 mL |

TABLE 6

Results for Pulsed Suction Column
Chromatography (pulse = 10 sec)

| Trial 1 | |
|---|---|
| Total time for fraction collection | 12 min |
| Number of fractions | 21 |
| Elution volume (weight) of Nmet | 50 mL (855 mg) |
| Elution volume (weight) of Acet | 225 mL (895 mg) |
| Total volume of eluent | 550 mL |
| One tube a mixture of Nmet + Acet = 25 mL | 25 mL (250 mg) |
| Trial 2 | |
| Total time for fraction collection | 12 min |
| Number of fractions | 20 |
| Elution volume (weight) of Nmet | 50 mL (850 mg) |
| Elution volume (weight) of Acet | 225 mL (770 mg) |
| Total volume of eluent | 500 mL |
| One tube a mixture of Nmet + Acet | 25 mL (350 mg) |

TABLE 7

Results for Pulsed Suction Column
Chromatography (pulse = 15 sec)

| Trial 1 | |
|---|---|
| Total time for fraction collection | 13 min |
| Number of fractions | 25 |
| Elution volume (weight) of Nmet | 125 mL (960 mg) |
| Elution volume (weight) of Acet | 325 mL (970 mg) |
| Total volume of eluent | 625 mL |
| Trial 2 | |
| Total time for fraction collection | 11 min |
| Number of fractions | 25 |
| Elution volume (weight) of Nmet | 100 mL (850 mg) |
| Elution volume (weight) of Acet | 325 mL (880 mg) |
| Total volume of eluent | 625 mL |
| One tube a mixture of Nmet + Acet | 25 mL (200 mg) |

TABLE 8

Results for Pulsed Suction Column
Chromatography (pulse = 20 sec)

| Trial 1 | |
|---|---|
| Total time for fraction collection | 10 min |
| Number of fractions | 20 |
| Elution volume (weight) of Nmet | 50 mL (850 mg) |
| Elution volume (weight) of Acet | 260 mL (650 mg) |
| Total volume of eluent | 600 mL |
| One tube a mixture of Nmet + Acet | 25 mL (400 mg) |
| Trial 2 | |
| Total time for fraction collection | 10 min |
| Number of fractions | 20 |
| Elution volume (weight) of Nmet | 75 mL (920 mg) |
| Elution volume (weight) of Acet | 250 mL (990 mg) |
| Total volume of eluent | 600 mL |

TABLE 9

Parameters that are Constant for all of
the Dry Vacuum Column Chromatography Runs

| | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Vacuum strength | 650 torr |
| Isocratic elution | 1:1 hexanes/EtOAc |

TABLE 10

Results for Dry Vacuum Column Chromatography

| Trial 1 | |
|---|---|
| Total time for fraction collection | 14 min |
| Number of fractions | 20 |
| Elution volume (weight) of Nmet | 100 mL (800 mg) |
| Elution volume (weight) of Acet | 325 mL (825 mg) |
| Total volume of eluent | 600 mL |
| One tube a mixture of Nmet + Acet | 25 mL (225 mg) |
| Trial 2 | |
| Total time for fraction collection | 13 min |
| Number of fractions | 20 |
| Elution volume (weight) of Nmet | 100 mL (980 mg) |
| Elution volume (weight) of Acet | 350 mL (970 mg) |
| Total volume of eluent | 575 mL |

TABLE 11

Parameters and Results for Dry Vacuum Column Chromatography
Runs (according to the Synthesis 2001 paper)[4]

| Parameters | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 2 g silica. |
| Amount of Silica | 18 g |
| Volume of each fraction collected | 25 mL |
| Vacuum strength | 650 torr |
| 5% v/v incremental increase in solvent composition (100% hexanes to 100% EtOAc) | |

TABLE 11-continued

Parameters and Results for Dry Vacuum Column Chromatography Runs (according to the Synthesis 2001 paper)[4]

| Changes in comparison with pulse vacuum chromatography | |
|---|---|
| Silica for Adsorption | 2 g instead of 4 g |
| Amount of Silica | 18 g instead of 36 g |
| Elution | gradient elution instead of isocratic elution |
| Trial 1 | |
| Total time for fraction collection | 21 min |
| Number of fractions | 20 |
| Elution volume (weight) of Nmet | 50 mL (750 mg) |
| Elution volume (weight) of Acet | 125 mL (650 mg) |
| Total volume of eluent | 500 mL |
| Three tubes a mixture of Nmet + Acet | 75 mL (500 mg) |
| Trial 2 | |
| Total time for fraction collection | 19 min |
| Number of fractions | 20 |
| Elution volume (weight) of Nmet | 50 mL (780 mg) |
| Elution volume (weight) of Acet | 125 mL (730 mg) |
| Total volume of eluent | 500 mL |
| Three tubes a mixture of Nmet + Acet | 75 mL (440 mg) |

TABLE 12

Parameters and Results for Dry Vacuum Column Chromatography Runs (according to the Synthesis 2001 paper)[4] using Modified Amounts of Silica

| Parameters | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Vacuum strength | 650 torr |
| 5% v/v incremental increase in solvent composition (100% hexanes to 100% EtOAc) | |
| Changes in comparison with Synthesis 2001 paper | |
| Silica for Adsorption | 4 g instead of 2 g |
| Amount of Silica | 36 g instead of 18 g |
| Trial 1 | |
| Total time for fraction collection | 24 min |
| Number of fractions | 20 |
| Elution volume (weight) of Nmet | 50 mL (880 mg) |
| Elution volume (weight) of Acet | 175 mL (920 mg) |
| Total volume of eluent | 500 mL |
| One tube a mixture of Nmet + Acet | 25 mL (150 mg) |
| Trial 2 | |
| Total time for fraction collection | 21 min |
| Number of fractions | 20 |
| Elution volume (weight) of Nmet | 75 mL (900 mg) |
| Elution volume (weight) of Acet | 150 mL (810 mg) |
| Total volume of eluent | 500 mL |
| One tube a mixture of Nmet + Acet | 25 mL (200 mg) |

TABLE 13

Parameters and Results for Pulsed (5 sec) Suction Column Chromatography with Gradient Elution Runs

| Parameters | |
|---|---|
| $R_f$ (1:1 hexanes/EtOAc) | Acet = 0.42 |
| | Nmet = 0.64 |

TABLE 13-continued

Parameters and Results for Pulsed (5 sec) Suction Column Chromatography with Gradient Elution Runs

| Mixture of Acet/Nmet | 2 g (1 g each) |
|---|---|
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Vacuum strength | 650 torr |
| 5% v/v incremental increase in solvent composition (100% hexanes to 100% EtOAc) | |
| Trial 1 | |
| Total time for fraction collection | 14 min |
| Number of fractions | 21 |
| Elution volume (weight) of Nmet | 125 mL (890 mg) |
| Elution volume (weight) of Acet | 175 mL (850 mg) |
| Total volume of eluent | 500 mL |
| One tube a mixture of Nmet + Acet | 25 mL (200 mg) |
| Trial 2 | |
| Total time for fraction collection | 14 min |
| Number of fractions | 21 |
| Elution volume (weight) of Nmet | 100 mL (910 mg) |
| Elution volume (weight) of Acet | 175 mL (770 mg) |
| Total volume of eluent | 500 mL |
| One tube a mixture of Nmet + Acet | 25 mL (250 mg) |

TABLE 14

Parameters and Results for Alternating Pressure Flash Chromatography Runs

| Parameters | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 26 g |
| Volume of each fraction collected | 25 mL |
| Pressure of nitrogen gas | 8 psi |
| Isocratic elution with 1:1 hexanes/EtOAc | |
| 5 sec nitrogen pressure forward, 5 sec pressure backwards | |
| Trial 1 | |
| Total time for fraction collection | 35 min |
| Number of fractions | 20 |
| Elution volume (weight) of Nmet | 50 mL (880 mg) |
| Elution volume (weight) of Acet | 275 mL (830 mg) |
| Total volume of eluent | 500 mL |
| Two tubes a mixture of Nmet + Acet | 50 mL (250 mg) |
| Trial 2 | |
| Total time for fraction collection | 30 min |
| Number of fractions | 20 |
| Elution volume (weight) of Nmet | 75 mL (850 mg) |
| Elution volume (weight) of Acet | 275 mL (760 mg) |
| Total volume of eluent | 550 mL |
| Three tubes a mixture of Nmet + Acet | 75 mL (300 mg) |

TABLE 15

Parameters and Results for Alternating Pressure Flash Chromatography Runs (Part 2)

| Parameters | |
|---|---|
| $R_f$ (1:1 hexanes/EtOAc) | Acet = 0.42 |
| | Nmet = 0.64 |

TABLE 15-continued

Parameters and Results for Alternating Pressure Flash Chromatography Runs (Part 2)

| | |
|---|---|
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Pressure of nitrogen gas | 8 psi |
| Isocratic elution with 1:1 hexanes/EtOAc | |
| 5 sec nitrogen pressure forward, 5 sec pressure backwards | |

Trial 1

| | |
|---|---|
| Total time for fraction collection | 35 min |
| Number of fractions | 20 |
| Elution volume (weight) of Nmet | 50 mL (960 mg) |
| Elution volume (weight) of Acet | 325 mL (960 mg) |
| Total volume of eluent | 550 mL |

Trial 2

| | |
|---|---|
| Total time for fraction collection | 30 min |
| Number of fractions | 20 |
| Elution volume (weight) of Nmet | 50 mL (940 mg) |
| Elution volume (weight) of Acet | 325 mL (920 mg) |
| Total volume of eluent | 550 mL |
| One tube a mixture of Nmet + Acet | 25 mL (100 mg) |

TABLE 16

Parameters and Results for Alternating Pressure Flash Chromatography Runs (Part 3)

Parameters

| | |
|---|---|
| $R_f$ (1:1 hexanes/EtOAc) | Acet = 0.42 |
| | Nmet = 0.64 |
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Pressure of nitrogen gas | 8 psi |
| Isocratic elution with 1:1 hexanes/EtOAc | |
| 10 sec nitrogen pressure forward, 10 sec pressure backwards | |

Trial 1

| | |
|---|---|
| Total time for fraction collection | 45 min |
| Number of fractions | 20 |
| Elution volume (weight) of Nmet | 25 mL (800 mg) |
| Elution volume (weight) of Acet | 325 mL (720 mg) |
| Total volume of eluent | 550 mL |
| Four tubes a mixture of Nmet + Acet | 100 mL (400 mg) |

Trial 2

| | |
|---|---|
| Total time for fraction collection | 40 min |
| Number of fractions | 20 |
| Elution volume (weight) of Nmet | 25 mL (825 mg) |
| Elution volume (weight) of Acet | 350 mL (815 mg) |
| Total volume of eluent | 550 mL |
| Three tubes a mixture of Nmet + Acet | 75 mL (350 mg) |

TABLE 17

Parameters and Results for Repetition of Gravity Column Chromatography with Less Silica Gel Parameters

| | |
|---|---|
| $R_f$ (1:1 hexanes/EtOAc) | Acet = 0.42 |
| | Nmet = 0.64 |

TABLE 17-continued

Parameters and Results for Repetition of Gravity Column Chromatography with Less Silica Gel

| | |
|---|---|
| Mixture of Acet/Nmet | 2 g (1 g each) |
| Application of mixture on silica | Dissolved in 7.5 mL EtOAc, sonicated for 1 min, adsorbed on 4 g silica. |
| Amount of Silica | 36 g |
| Volume of each fraction collected | 25 mL |
| Isocratic elution with 1:1 hexanes/EtOAc | |

Trial 1

| | |
|---|---|
| Total time for fraction collection | 78 min |
| Number of fractions | 20 |
| Elution volume (weight) of Nmet | 50 mL (930 mg) |
| Elution volume (weight) of Acet | 275 mL (810 mg) |
| Total volume of eluent | 600 mL |
| Two tubes a mixture of Nmet + Acet | 50 mL (160 mg) |

Trial 2

| | |
|---|---|
| Total time for fraction collection | 71 min |
| Number of fractions | 20 |
| Elution volume (weight) of Nmet | 75 mL (880 mg) |
| Elution volume (weight) of Acet | 275 mL (850 mg) |
| Total volume of eluent | 625 mL |
| One tube a mixture of Nmet + Acet | 25 mL (100 mg) |

TABLE 18

Comparison of Separation Methods[a]

| | Gravity | Flash | Vacuum, Time-Pulsed[b] | | Pressure, Time-Pulsed[c] | |
|---|---|---|---|---|---|---|
| Silica (g) | 150 | 36 | 150 | 36[d] | 36[e] | 36[f] | 36[g] |
| No. of fractions | 38[h1] | 20[h2] | 36[i] | 20[j] | 20[k] | 20[l] | 20[m] |
| Solvent (mL) | 1140 | 615 | 1065 | 510 | 525 | 550 | 550 |
| Time (min) | 73 | 75 | 38 | 14 | 12 | 32 | 43 |

[a]Average of several trials
[b]The pump used generated 650 mmHg, hence a reverse ΔP gradient of ~100 mmHg
[c]The nitrogen pressure was 8 psi
[d]5 second pulse
[e]10 second pulse
[f]5 second alternating pulse
[g]10 second alternating pulse
[h1]Fraction volume = 30 mL
[h2]Fraction volume = 25 mL
[i]Fraction volume = 30 mL
[j]Fraction volume = 25 mL
[k]Fraction volume = 25 mL
[l]Fraction volume = 25 mL
[m]Fraction volume = 25 mL

The invention claimed is:

1. A method for liquid chromatographic separation of two or more sample components comprising:
   a) introducing a sample comprising the two or more sample components into an inlet of a column containing a stationary phase;
   b) applying at least one time-pulsed pressure differential to the sample within the column comprising the steps of:
      i) applying a first pressure to the sample to cause the sample to flow past the stationary phase in a first flow direction; and
      ii) after step i), applying a second pressure that is different than the first pressure to the sample to cause the sample to reverse flow direction within the column and flow past the stationary phase in an opposite, second flow direction;
      iii) after step ii) causing the sample to resume flowing in the first flow direction; and c) obtaining a sample rich liquid mobile phase from an outlet of the column.

2. The method of claim 1 comprising:
b) obtaining the sample rich liquid mobile phase in step c) while applying the at least one time-pulsed pressure differential to the column in step b).

3. The method of claim 1, wherein:
step i) comprises applying a vacuum to the column using a vacuum source coupled to the column at a position below the stationary phase;
step ii) comprises releasing the vacuum applied to the column; and
step iii) comprises reapplying the vacuum to the column.

4. The method of claim 3, wherein:
step i) comprises applying a first positive pressure to the column at a position above the stationary phase;
step ii) comprises stopping the first positive pressure applied to the column and applying a second positive pressure to the column at a position below the stationary phase;
step iii) comprises stopping the second positive pressure applied to the column and reapplying the first positive pressure applied to the column.

5. The method of claim 4, further comprising applying the first positive pressure with a first pressure source and applying the second positive pressure with at least one of the first pressure source and a second pressure source.

6. The method of claim 5, comprising applying the second positive pressure with the second pressure source.

7. The method of claim 6, wherein each of the first pressure source and the second pressure source comprise a source of pressurized inert gas.

8. The method of claim 4, further comprising repeating steps i) to iii) of claim 1 until separation of the two or more sample components is at least substantially complete.

9. The method of claim 4, further comprising repeating steps i) to iii) of claim 1 until each of the two or more sample components has eluted from the stationary phase and a peak separation between each of the two or more sample components is at least about 90%.

10. The method of claim 3, wherein the vacuum applied in step a) is between about 450 mm Hg to about 650 mm Hg.

11. The method of claim 3, wherein releasing the vacuum causes a pressure shockwave to travel upwardly through the stationary phase.

12. The method of claim 3, further comprising repeating steps i) to iii) of claim 1 until separation of the two or more sample components is at least substantially complete.

13. The method of claim 3, further comprising repeating steps i) to iii) of claim 1 until each of the two or more sample components has eluted from the stationary phase and a peak separation between each of the two or more sample components is at least about 90%.

14. The method of claim 1, wherein at least one of i) and iii) are run for a time of about 3 seconds to about 10 seconds, and ii) is run for a time of about 5 seconds to about 15 seconds.

15. The method of claim 1, wherein applying the at least one time-pulsed pressure differential to the column is automatically controlled.

16. The method of claim 15, wherein a programmable controller automatically controls applying the at least one time-pulsed pressure differential to the column.

17. The method of claim 1, wherein the sample is introduced into the inlet of the column as a composition comprising the sample adsorbed to an adsorbent, the adsorbent having the same composition as the stationary phase.

18. The method of claim 1, further comprising collecting one or more fractions of the sample rich liquid mobile phase.

19. The method of claim 1, wherein the stationary phase comprises silica gel.

20. The method of claim 1, wherein
step i) comprises applying a negative pressure to the column using a vacuum source fluidly coupled to the column at a position below the stationary phase;
step ii) comprises releasing the negative pressure after a first predetermined time interval and allowing the pressure applied to the sample increases from the first pressure to the second pressure; and
step iii) comprises reapplying the negative pressure to the column after a second predetermined time interval and whereby the pressure applied to the sample decreases from the first pressure to the second pressure.

* * * * *